(12) United States Patent
Heffner et al.

(10) Patent No.: US 6,316,764 B2
(45) Date of Patent: Nov. 13, 2001

(54) AUTOALIGNMENT AND AUTOFOCUS MECHANISM FOR COUPLING LIGHT BETWEEN AN OPTICAL FIBER AND A PHYSICAL SPECIMEN

(75) Inventors: Brian L. Heffner, Los Altos; Wayne V. Sorin, Mountain View, both of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/783,571

(22) Filed: Feb. 12, 2001

Related U.S. Application Data

(63) Continuation of application No. 08/556,890, filed on Nov. 2, 1995, now Pat. No. 6,215,118.

(51) Int. Cl.$^7$ .................................................. G01J 1/104
(52) U.S. Cl. .................................. 250/227.11; 250/201.1; 369/44.13
(58) Field of Search ........................... 250/227.11, 221.3, 250/201.1, 216, 201.5; 369/44.13, 44.22; 356/477

(56) References Cited

U.S. PATENT DOCUMENTS 4,358,774 * 11/1982 Wilkinson ........................ 369/44.13
4,445,209 * 4/1984 Mickleson et al. ............... 250/201.5

* cited by examiner

Primary Examiner—John R. Lee
Assistant Examiner—Kevin Pyo

(57) ABSTRACT

An apparatus for applying an optical signal to a surface and collecting the light leaving the surface in response to the application of the optical signal. The optical signal and the collected light traverse an optical fiber having an end proximate to the surface which delivers light to the surface with the aid of a lens that couples the optical signal to the surface, collects the light emitted by the surface, and couples collected light into the optical fiber. A detector measures the intensity of light delivered into the optical fiber and generates a detection signal indicative of the measured intensity as a function of time. A set of actuators dither the position of the lens relative to the proximate end of the fiber. Each actuator operates at a different dither frequency and moves the lens relative to fiber along a different axis. The average position of the lens relative to the proximate end of the fiber along each axis is adjusted so as to maximize the average power detected at the corresponding dither frequency.

2 Claims, 4 Drawing Sheets

AUTOALIGNMENT AND AUTOFOCUS MECHANISM FOR COUPLING LIGHT BETWEEN AN OPTICAL FIBER AND A PHYSICAL SPECIMEN

CROSS REFERENCE TO RELATED APPLICATION(S)

This is a continuation of application Ser. No. 08/556,890 filed on Nov. 2, 1995, and now U.S. Pat. No. 6,215,118.

FIELD OF THE INVENTION

The present invention relates to fiber optic systems, and more particularly, to an improved mechanism for coupling a fiber to a specimen such that light reflected back by the specimen is efficiently collected in the optical fiber.

BACKGROUND OF THE INVENTION

There are numerous physical measurements that attempt to deduce a property of a sample by observing the light reflected from the sample when the sample is illuminated with light. For example, information about the chemical composition of a sample can often be deduced by observing the fluorescent spectrum induced by illuminating the specimen with light of a known wavelength.

To make such measurements, light must be conducted to the specimen and the light emitted therefrom collected for analysis. Single and multimode optical fibers are often used to deliver the light to the specimen. Such fibers are easily manipulated and have high transmission over a considerable bandwidth. In principle, the same fiber can be used to collect the light leaving the specimen. While this type of collection scheme provides an attractive solution to the light collection problem, it functions poorly in those cases in which the position and/or tilt of the specimen changes during the measurement process.

A number of measurement applications are designed to measure the properties of a moving specimen. For example, interferometric techniques can be utilized to measure the thickness and composition of thin films as the films are manufactured. Unfortunately, the films are moving at relatively high speeds and tend to "flutter". The flutter results in changes in angle and/or distance of the film relative to the optical fiber used to deliver light to the film and collect the light reflected back by the front and back surfaces of the film.

Typically, a lens is used to couple the light between the optical fiber and the surface. There are two common lens configurations, collimating and imaging. In a collimating configuration, the light leaving the fiber is expanded into a beam of parallel rays having a diameter much larger than the optical fiber core. Light that returns parallel to the direction of the original ray bundle will be focused by the lens back into the optical fiber. If the tilt of the surface changes, this condition will not be satisfied, and hence, the collection efficiency will be poor. The distance between the lens and the surface has only a weak effect on the collection efficiency. Hence, the collimating configuration is insensitive to movement of the surface along the beam directions.

In the imaging configuration, the lens is used to form an image of the fiber core on the specimen. The specimen is thus illuminated at a point. This configuration is relatively insensitive to tilting of the specimen. However, changes in the distance between the lens and the specimen result in the illuminated spot on the specimen expanding. Since imaging of the illuminated spot back into the fiber depends upon the correct spacing between the lens and the specimen, the efficiency of light collection in the imaging configuration is very sensitive to changes in the distance between the lens and the specimen.

Broadly, it is the object of the present invention to provide an improved alignment system for optical coupling lens system used in coupling light from an optical fiber to a specimen.

It is a further object of the present invention to provide an alignment system that can correct for changes in orientation of the specimen surface.

It is a still further object of the present invention to provide an alignment system that can correct for changes in distance between the lens system and the specimen surface.

These and other objects of the present invention will become apparent to those skilled in the art from the following detailed description of the invention and the accompanying drawings.

SUMMARY OF THE INVENTION

The present invention comprises an apparatus for applying an optical signal to a surface and collecting the light leaving the surface in response to the application of the optical signal. The optical signal and the collected light traverse an optical fiber having an end proximate to the surface which delivers light to the surface with the aid of a lens that couples the optical signal to the surface, collects the light emitted by the surface, and couples collected light into the optical fiber. A detector measures the intensity of light delivered into the optical fiber and generates a detection signal indicative of the measured intensity as a function of time. A set of actuators dither the position of the lens relative to the proximate end of the fiber. Each actuator operates at a different dither frequency and moves the lens relative to fiber along a different axis. The average position of the lens relative to the proximate end of the fiber along each axis is adjusted so as to maximize the average power detected at the corresponding dither frequency.

DETAILED DESCRIPTION OF THE INVENTION

Figure 1:
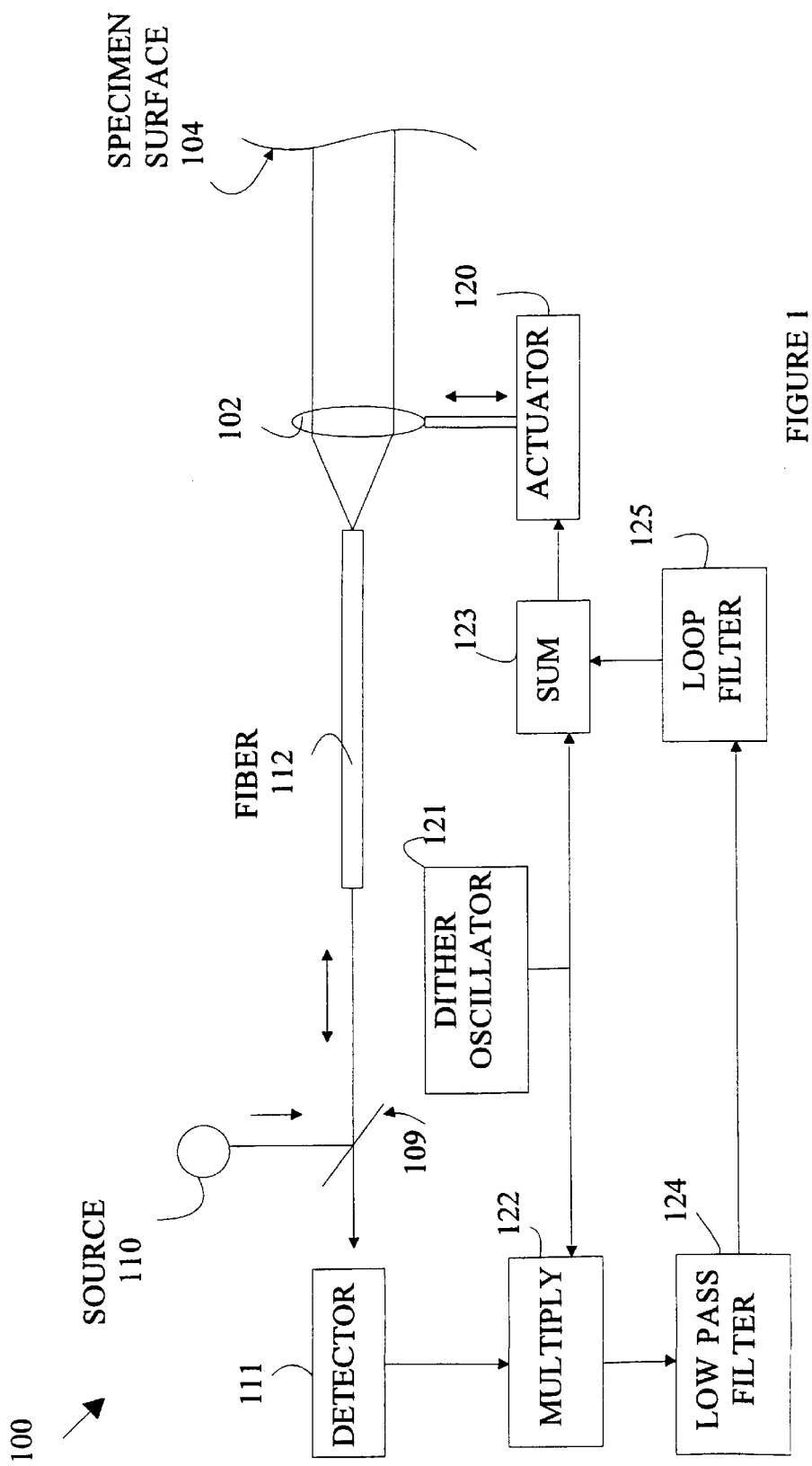
FIG. 1 is a block diagram of motion compensation system according to the present invention for controlling the relative position of a lens and optical fiber in one dimension.

The method by which the present invention obtains its advantages may be more easily understood with reference to FIG. 1 which is a block diagram of motion compensation system 100 according to the present invention which uses a dither oscillator 121 to vary the position of a lens 102 with respect to the end of fiber 112. For the purposes of this example, it is assumed that the specimen surface is tilting during the measurement. The specimen is illuminated with light from a source 110 which is delivered to the specimen via fiber 112. Lens 102 collimates the light leaving fiber 112 and collects the light returning from the specimen surface. The intensity of the collected light is measured with the aid of detector 111.

System 100 generates a signal that positions lens 102 such that the maximum amount of light is returned to detector 111 when the mean value of the output of low pass filter 124 is zero. This is accomplished by dithering the lens back and forth as shown in the drawing. The detected power will thus vary with time. The output of the detector is multiplied via circuit 122 by the dither frequency which has a mean value of zero. This generates a signal with a mean value that is proportional to the deviation of the mean lens position from the ideal position. The mean value is extracted with the aid of low pass filter 124. This signal is used as an error signal input to loop filter 125 which provides an offset to the actuator position necessary to reduce the output of filter 124 to zero.

Figure 2:
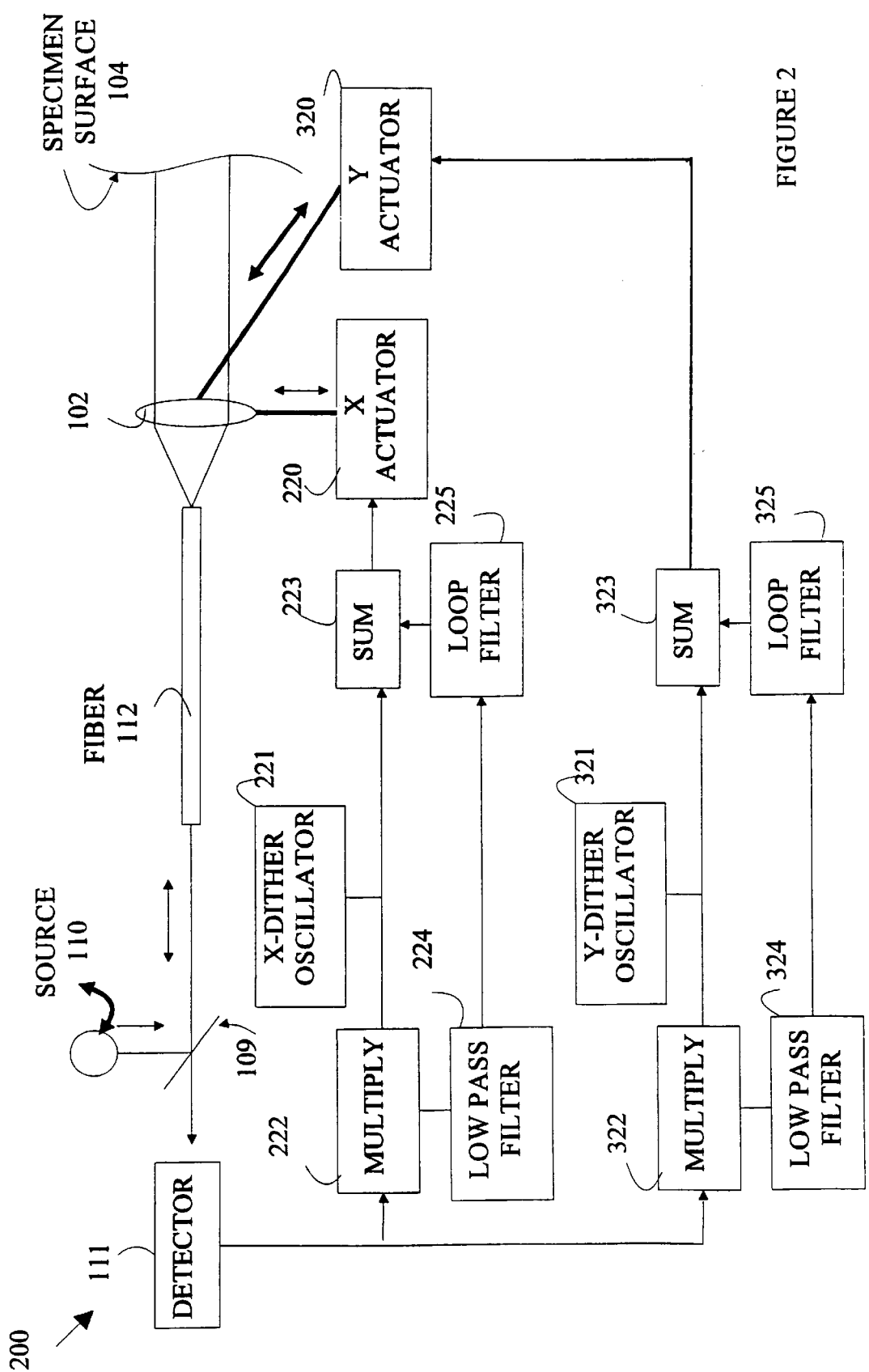
FIG. 2 is a block diagram of motion compensation system according to the present invention for controlling the relative position of a lens and optical fiber in two dimensions.

In the case of a collimating geometry such as shown in FIG. 1, the lens need only be aligned in a plane perpendicular to the axis of fiber 112. Alignment in two dimensions can be accomplished by utilizing a second actuator to move the lens in a direction orthogonal to actuator 120. The second actuator is driven by a second dither oscillator driven at a different frequency. The use of different dither frequencies allows the x and y controls to be operated separately without one interfering with the other. The multiplication circuits effectively limit each servo loop to the frequency of the oscillator in that loop. Such an arrangement is shown in FIG. 2 at 200 which is a block diagram of a two dimensional dither servo system for positioning lens 102 in the x-y plane. Motion in the x-direction is accomplished via actuator 220 and in the y-direction via actuator 320. The x-actuator is controlled by a first servo loop comprising dither oscillator 221, multiplier 222, low pass filter 224, loop filter 225, and sum circuit 223. Similarly, the y-actuator is controlled by a second servo loop comprising dither oscillator 321, multiplier 322, low pass filter 324, loop filter 325, and sum circuit 323.

Actuators constructed from voice coils are common in the art and suitable for the implementation of the actuators 220 and 320 described above. Since such actuators are well known to those in the mechanical arts they will not be discussed further here.

In systems utilizing an imaging lens, a third servo loop utilizing a third dither frequency may be implemented to move the lens parallel to the fiber axis. Since such geometries are similar to that shown in FIGS. 1 and 2, the 3-dimensional servo system will not be discussed further here.

Figure 3:
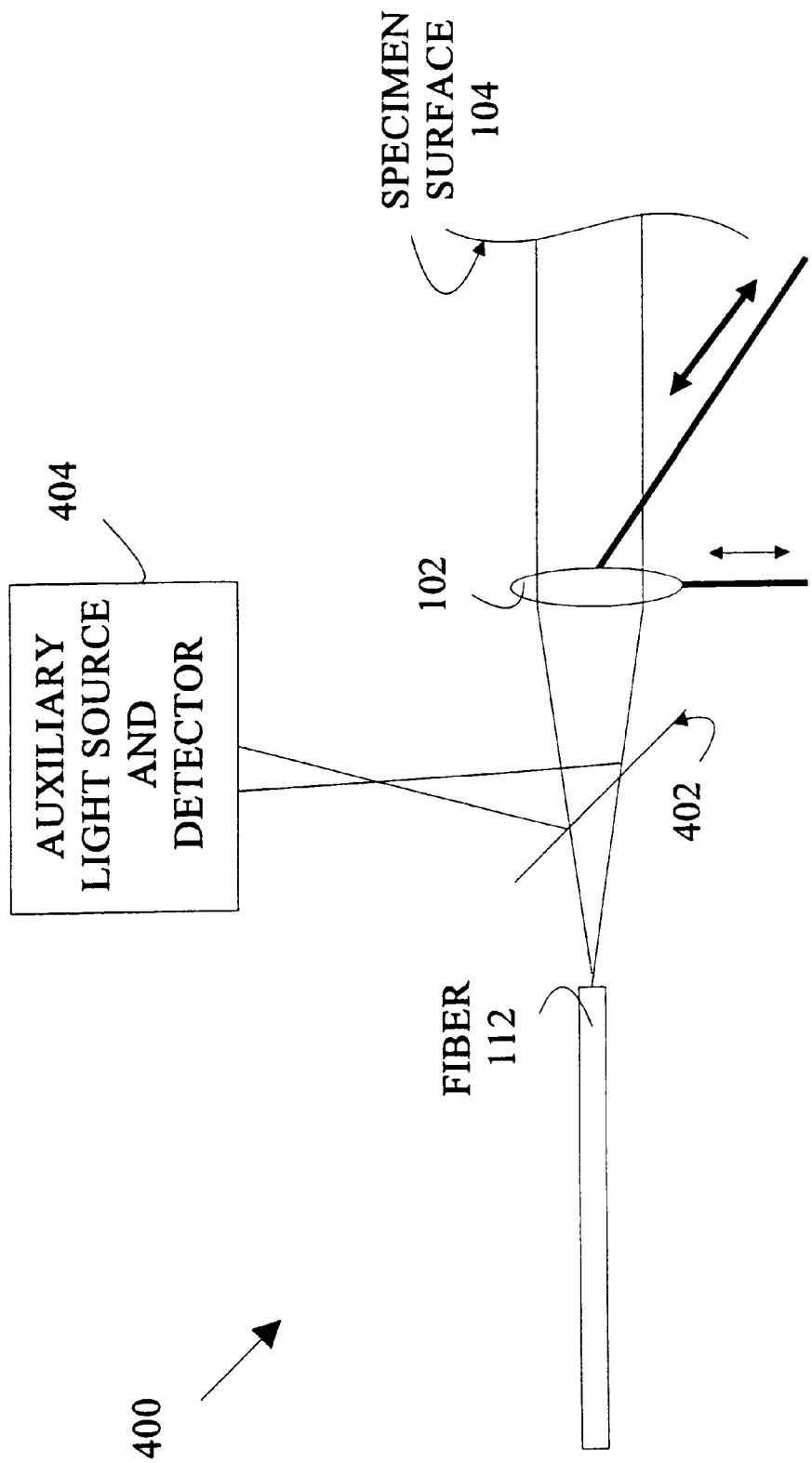
FIG. 3 is illustrates an alternative placement of the light source and detector used to maintain the position of the lens relative to the fiber.

One disadvantage of the system discussed above is the use of the detector output to generate the servo signals. In some cases, the detector output is not conveniently available, as it is part of a commercial measurement system that may be located at some distance from the specimen. In such situations, a second detector and/or light source may be utilized as shown at 400 in FIG. 3. A beam splitter 402 is introduced between the end of fiber 112 and lens 102. The auxiliary illumination system and detector 404 can then be coupled to the system via this beam splitter. It should be noted that both the auxiliary light source and auxiliary detector need not be placed off of the beam splitter. For example, systems in which only the auxiliary detector is run from the beam splitter will be apparent to those skilled in the art. In such a system, the auxiliary light source may be located at the instrument detector or be absent altogether.

Figure 4:
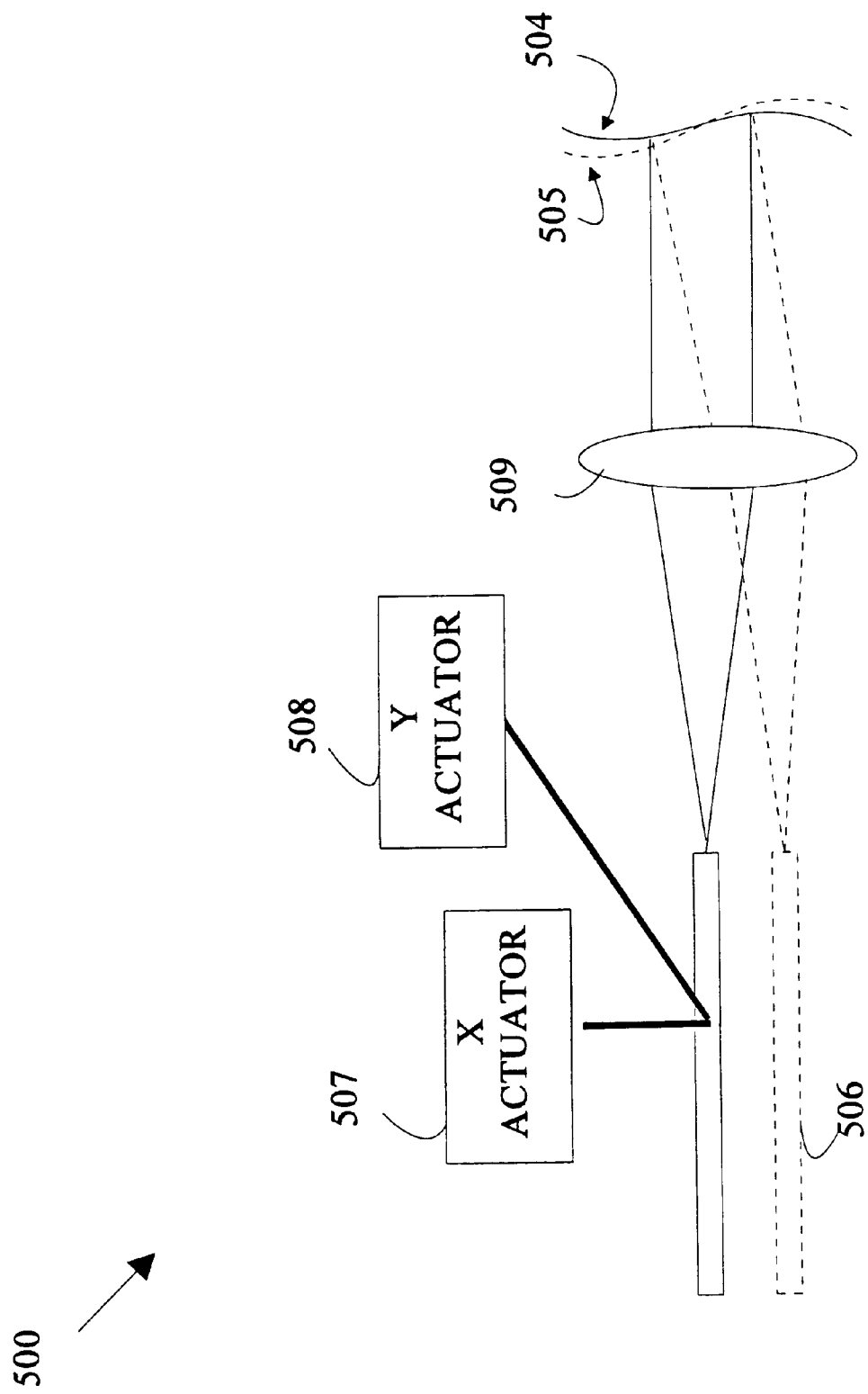
FIG. 4 is a block diagram of a system according to the present invention in which the lens is fixed relative to the surface being examined while the end of the optical fiber is moved.

While the above arrangement controls the position of the lens, alternate embodiments in which the position of the fiber end is moved relative to the lens may also be constructed according to the teachings of the present invention. In one such system, the actuators are connected to the fiber end and the lens remains fixed. Such systems are preferred in measurement systems in which the position that is illuminated on the specimen must not change. Loss of reflective coupling caused by tilt of the specimen can be corrected by moving the fiber end to the new location as shown in FIG. 4. When the specimen tilts from the configuration shown at 504 to that shown at 505, the beam moves to a new location which necessitates the movement of the end of the fiber to the new position shown at 506. This can be accomplished using the same servo system discussed above with the actuators 507 and 508 connected to the fiber end.

It should be noted that the working distance between the specimen and lens 504 may be increased by replacing lens 509 shown in FIG. 4 with a suitable combination of lenses that provides the desired working distance. In particular, a combination of lenses can be designed to provide a long working distance and, at the same time, allow use of actuators with limited range of mechanical motion. Such arrangements are conventional in the optical arts, and hence, will not be discussed in more detail here.

Various modifications to the present invention will become apparent to those skilled in the art from the foregoing description and accompanying drawings. Accordingly, the present invention is to be limited solely by the scope of the following claims.

What is claimed is:

1. An apparatus for applying an optical signal to a surface and collecting the light emitted by said surface in response to said application of said optical signal, said optical signal and said collected light traversing an optical fiber having an end proximate to said surface, said apparatus comprising:

a lens for coupling said optical signal to said surface and for collecting said light emitted by said surface and coupling said collected light into said optical fiber;

a detector for measuring the intensity of light collected in said optical fiber and for generating a detection signal indicative of said measured intensity as a function of time; and means for moving one of said lens and said optical fiber relative to the other at a first frequency back and forth along a first axis, said lens having an average position relative to said optical fiber along said first axis controlled by said moving means, said average position being repetitively adjusted to maximize the average power of said detection signal at said first frequency, wherein said first axis is perpendicular to the axis of said lens.

2. The apparatus of claim 1 further comprising:

a beam splitter between said proximate end of said optical fiber and said lens, said beam splitter directing a portion of said light collected by said lens to said detector.

* * * * *